United States Patent [19]

Israel et al.

[11] Patent Number: 5,016,661
[45] Date of Patent: May 21, 1991

[54] APPARATUS FOR HOLDING DENTAL FLOSS CONTAINERS

[76] Inventors: Gina Israel, 555 Cornelia #1601, Chicago, Ill. 60657; Bonnie S. LaRussa, 234 N. Rose Ave., Park Ridge, Ill. 60068

[21] Appl. No.: 225,775
[22] Filed: Jul. 29, 1988
[51] Int. Cl.$^5$ .............................................. A61C 15/00
[52] U.S. Cl. ..................... 132/324; 132/325; 206/63.5; 206/409
[58] Field of Search ............... 132/321, 323, 324, 325, 132/326, 327, 328, 329; 206/63.5, 409; 220/410; 221/31, 64, 66, 197, 198, 287, 307, 309, 310, 312 C; 211/65

[56] References Cited

U.S. PATENT DOCUMENTS

| | | | |
|---|---|---|---|
| 1,455,673 | 5/1923 | Shalek | 132/325 |
| 2,893,405 | 7/1959 | Castelli | 132/321 |
| 2,929,541 | 3/1960 | Castelli et al. | 132/321 |
| 3,789,859 | 2/1974 | Chambers | 132/326 |
| 3,830,247 | 8/1974 | Kaphalakos | 132/325 |
| 4,140,222 | 2/1979 | Francavilla | 211/65 |
| 4,178,947 | 12/1979 | McCourry et al. | 132/324 |
| 4,286,611 | 9/1981 | Talbot | 132/321 |
| 4,753,254 | 6/1988 | McCullough et al. | 132/324 |
| 4,844,104 | 7/1989 | Martin | 132/321 |

Primary Examiner—John J. Wilson
Assistant Examiner—F. LaViola
Attorney, Agent, or Firm—Patula & Associates

[57] ABSTRACT

A dental floss container holder and floss dispenser having a housing with a front and back portion. A contoured resilient material made of closed or open cell foam or neoprene for retaining variously shaped dental floss containers and spools. The retaining material is affixed to the interior of the housing. A guide directs floss from the retained container to the exterior of the housing. A cutter is positioned on the exterior of the housing. The housing may be wall mountable.

18 Claims, 4 Drawing Sheets

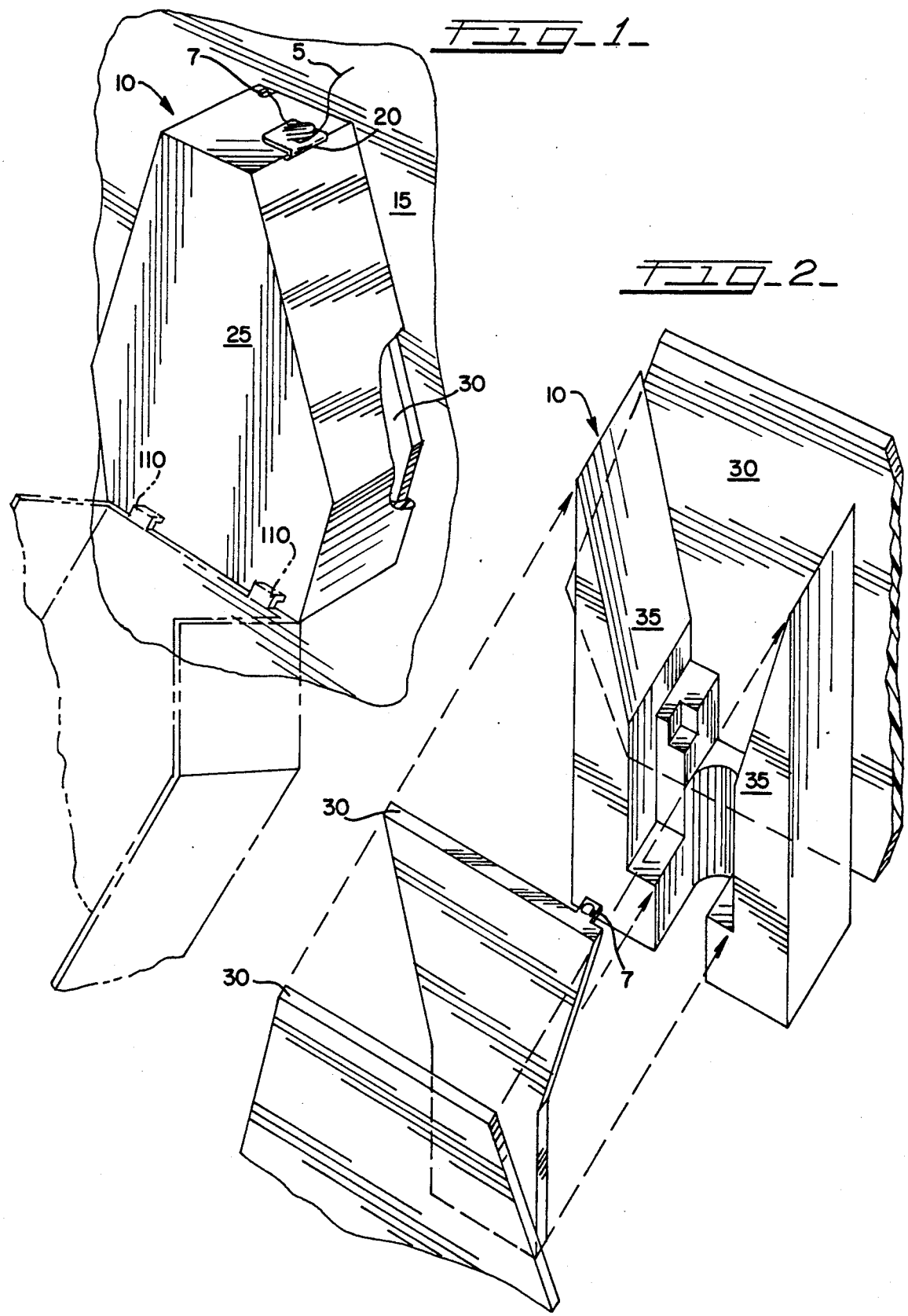

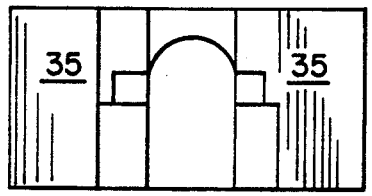
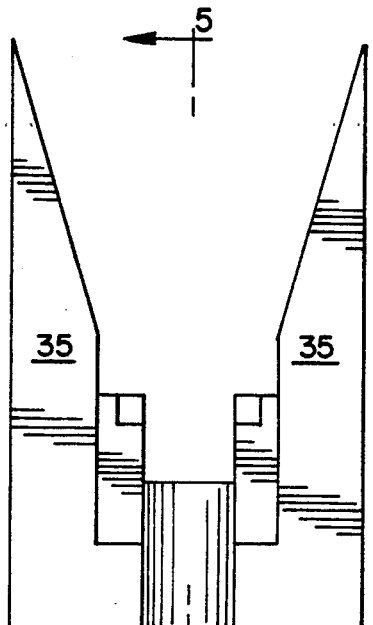
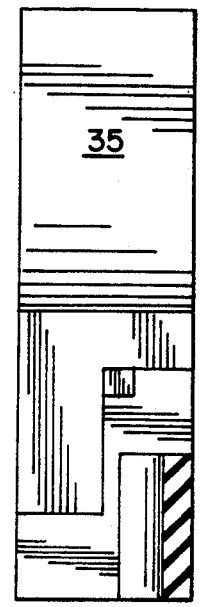
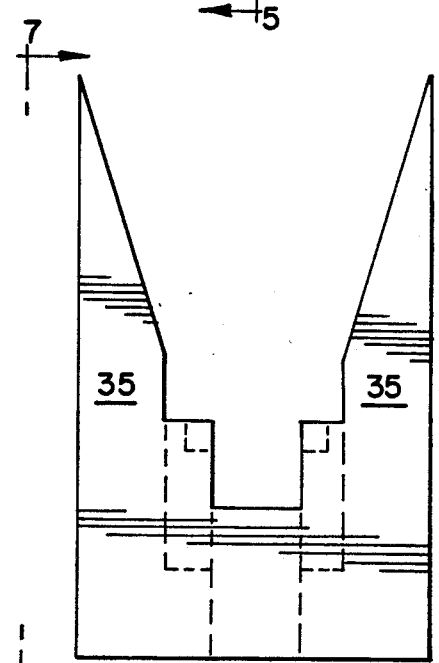
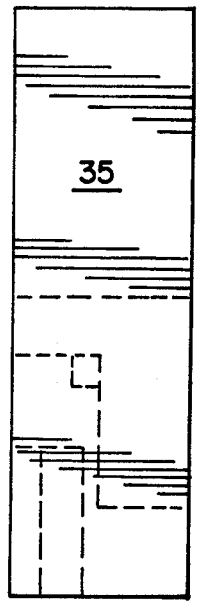
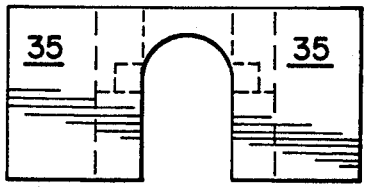

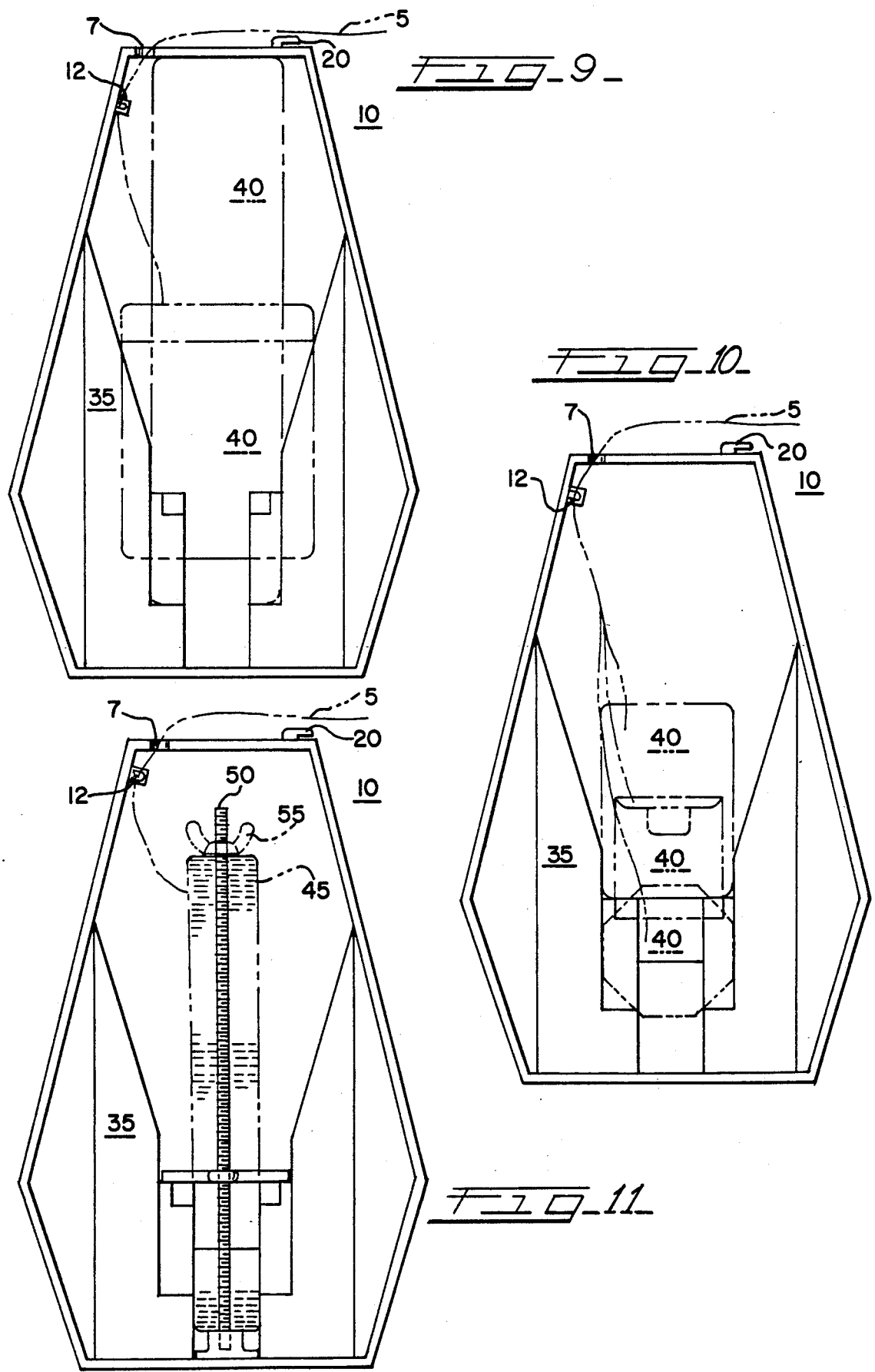

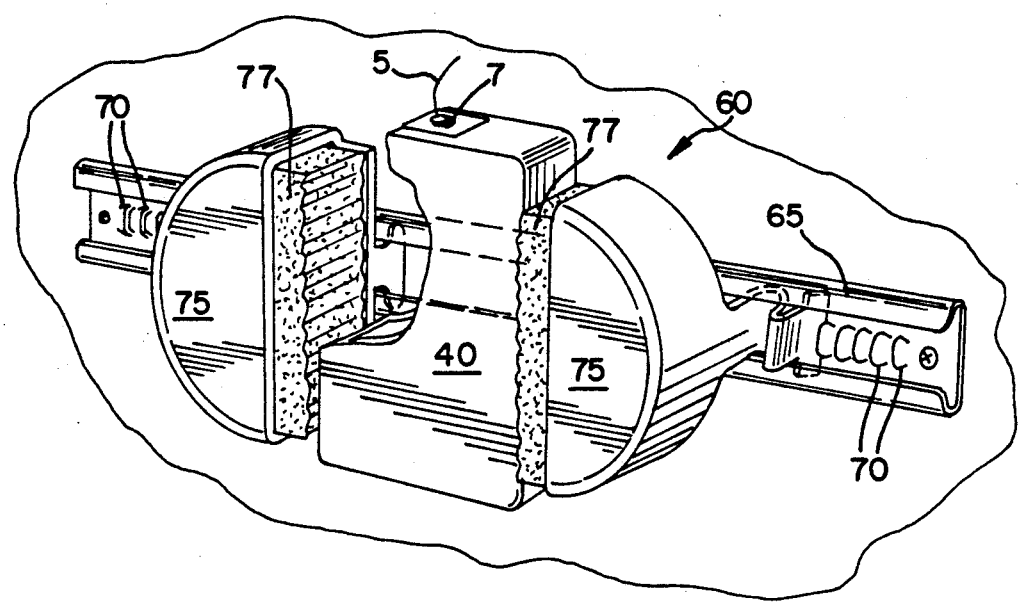
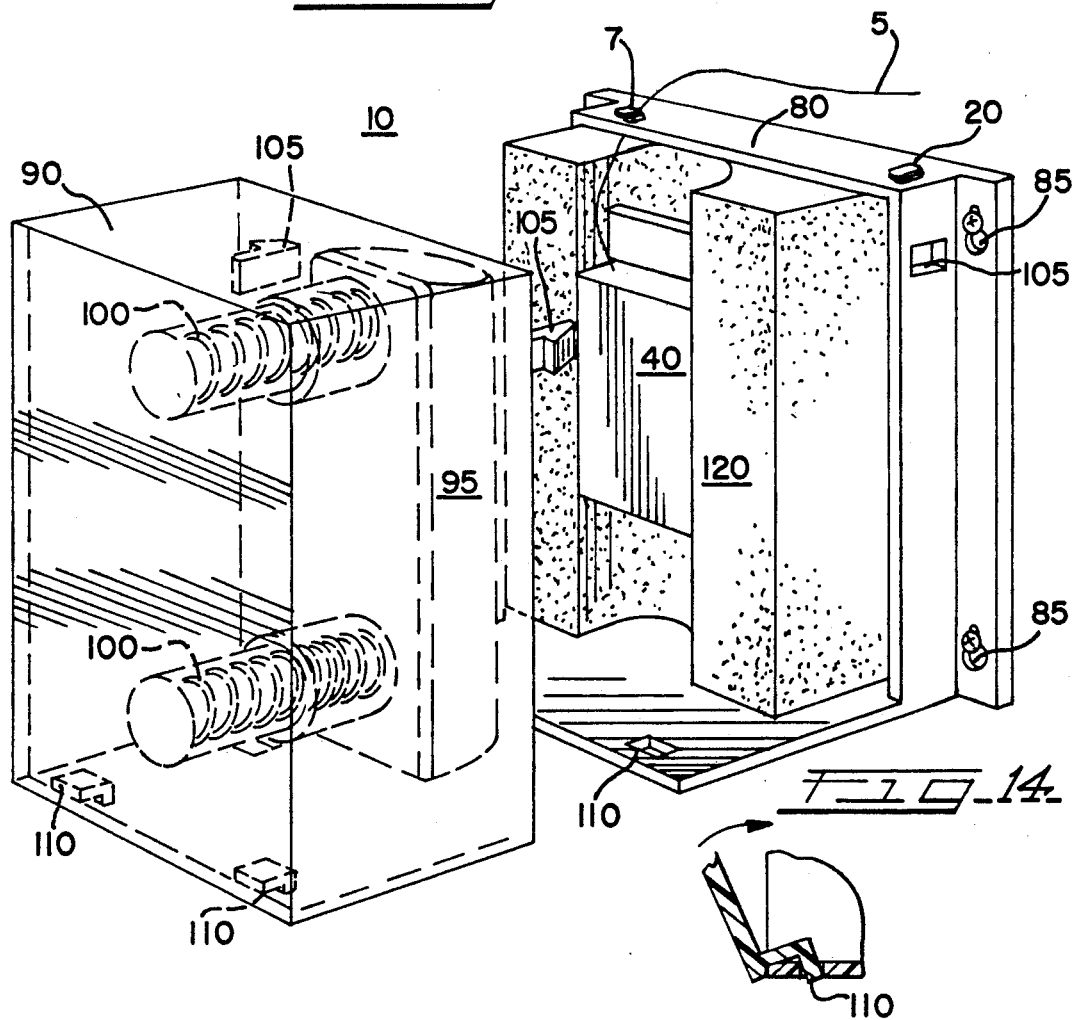

APPARATUS FOR HOLDING DENTAL FLOSS CONTAINERS

This invention relates specifically to the supporting and dispensing of dental floss either in spools or from variously sized and shaped containers available in the marketplace.

It is a well known fact that daily and consistent use of dental floss for removing bacterial plaque in proximity to the gums and between the teeth is recommended by dental authorities in the furtherance of good oral hygiene practice. One of the ways in order to induce the use of dental floss is by making the floss handy and convenient to use at various locations. The fact that most dental floss containers are hidden away in a medicine cabinet or bathroom drawer prevents the user from using dental floss daily.

The present invention solves the need for a suitable reminder to stimulate the user to utilize dental floss.

BACKGROUND OF THE INVENTION

Various types of dental floss dispensing devices have been known in the past including devices having various features which are attractive to children and adults. U.S. Pat. No. 4,308,880 to Craves discloses an animated dental floss dispenser which simulates the flossing of a person's teeth with the simultaneous dispensing of a dental floss. U.S. Design Pat. Nos. 176,090, 154,894 and 76,490 disclose various ornamental designs for dental floss holders.

U.S. Pat. No. 2,967,651 to Zackheim etal discloses a font for dispensing dental floss but teaches nothing in regard to holding variously sized dental floss containers.

U.S. Pat. No. 2,929,541 to Castelli etal discloses a dispenser for dental floss and other filaments which requires a specific spool type shape to be held for dispensing thereof which is limited only to that shape spool.

U.S. Pat. No. 3,789,859 to Chambers discloses a dental floss holder which holds a spool of floss in a taunt position between a pair of spaced prongs for dispensing. Although this device holds two different types of dental floss spools, it is not a universal type device for containing various size containers.

U.S. Pat. No. 1,455,673 to Shalek discloses a wall mounted dental floss dispenser which holds only a single specific shape dental floss spool. The present invention is adaptable to receive and dispense floss from all types and shapes of floss containers.

The above references all have various shortcomings which the present invention obviates. Many of the above floss holders are unable to receive and dispense dental floss housed in various commercially available shaped containers or floss on spools without containers. The present invention as shown in the following embodiments, allow numerous shaped containers and spools to be housed and then readily dispensed for use.

SUMMARY OF INVENTION

A wall mountable apparatus for holding dental floss containers and spools having in the preferred embodiment a series of simultaneous contours and cutouts in order to receive and retain variously shaped dental floss containers and spools. Other embodiments include a clamp like bracket for grasping the floss container, an axial spool or bobbin support and a universal cavity for supporting non-uniform and uniform dental floss containers and spools. Each of the embodiments disclosed will readily dispense the floss contained and because of their vertical surface or counter top mountability, serve as a reminder to floss daily due to the constant visibility of the present invention.

It is the principal object of the present invention to provide a dental floss holder which will accommodate all sizes and shaped containers of dental floss as well as those without containers which are contained on spools.

It is a further object of the present invention to provide a dental floss holder which will receive commercially available containers of floss without having to remove the floss contained for mounting into the invention.

It is a further object of the present invention to dispense dental floss with a simple mechanism having few working parts.

It is another object of the present invention that the apparatus hold the floss in a hygienic and sanitary manner.

It is yet another object of the present invention that the apparatus safely afford the portioned dispensing of floss to small children.

It is yet another object of the invention to provide a suitable housing and dispenser for dental floss that is aesthetically pleasing and corresponds with the surrounding decor.

Numerous other advantages and features of the invention will become readily apparent from the following detailed description of the preferred embodiment of the invention, from the claims, and from the accompanying drawings, in which like numerals are employed to designate like parts throughout the same.

BRIEF DESCRIPTION OF THE DRAWINGS

A fuller understanding of the foregoing will be had by reference to the accompanying drawings wherein:

FIG. 1 is a perspective view of the preferred embodiment of the apparatus for holding dental floss mounted on a vertical surface;

FIG. 2 is an internal perspective view of the preferred embodiment of FIG. 1;

FIG. 3 is a rear elevational view of the contoured internal retainer of the preferred embodiment of FIG. 1;

FIG. 4 is a top plan rear view of the contoured internal retainer of the preferred embodiment of FIG. 1;

FIG. 5 is a side elevational view along line 5—5 of FIG. 3;

FIG. 6 is a front elevational view of the contoured internal retainer of the preferred embodiment of FIG. 1;

FIG. 7 is a side elevational view along line 7-7 of FIG. 6;

FIG. 8 is a bottom plan view of the preferred embodiment of FIG. 1;

FIG. 9 is a rear cross-sectional view of the preferred embodiment receiving variously shaped floss containers;

FIG. 10 is a rear cross-sectional view of the preferred embodiment supporting various shaped floss containers;

FIG. 11 is a rear cross/sectional view of the preferred embodiment for receiving a cylindrical spool;

FIG. 12 is a perspective view of a clamp-type embodiment of the present invention;

FIG. 13 is a perspective view of a universal cavity-type embodiment of the present invention; and FIG. 14 is a side view of the fastening hinge for the universal cavity-type embodiment of the present invention.

DESCRIPTION OF PREFERRED EMBODIMENT

While this invention is susceptible of embodiment in many different forms, there is shown in the drawings and will herein be described in detail a number of embodiments of the invention. The invention disclosed herein is equally applicable to many other shaped and housed dental floss containers besides the embodiments shown and described herein. It should be understood that the present disclosure is to be considered an exemplification of the principles of the invention and is not intended to limit the spirit and scope of the invention and/or claims to the embodiments illustrated.

Referring now to the figure drawings, FIG. 1 is a perspective view of one of the preferred embodiments of the apparatus 10 for holding dental floss 5 mounted on a vertical surface 15. Vertical surface 15 in a practical home application, may be a bathroom wall. Likewise, other vertical surface applications such as oral hygienist, dentist or other dental professionals offices' are also appropriate. A dispensing opening 7 and cutting means 20 are positioned on the uppermost portion of the apparatuses' front housing 25. Said front housing 25 is hinged or fingered and slotted 110 at the base to allow internal access to the apparatus 10. Rear wall 30 is shown only in partial view.

Shown in FIG. 2 is a contoured internal cavity 35 formed of a resilient material within apparatus 10. The resilient material may be of conventional material such as open or closed cell foam or neoprene, known for its shape retention and its gripping ability to receive and support currently available variously shaped dental floss containers 40. The cavity 35 depicted in phantom lines of FIGS. 9 and 10 allows various dental floss containers 40 to be received and retained by the resilient material.

FIG. 11 depicts a cylindrical spool embodiment with a threaded shaft 50 axially positioned and supporting a spool of dental floss 45 and retained by a thumb screw 55.

FIG. 12 depicts the apparatus 10 of the present invention as a clamp-type holder of dental floss containers which receive and retain the container 40 as shown.

FIG. 13 depicts the apparatus 10 having a universal chamber with spring biased retaining means.

Guide 12 is further shown in FIGS. 9-11.

Shown in FIGS. 4-8 are various views of the contoured cut-outs of the cavity 35 for apparatus 10. The conception of the various contours in the preferred embodiment is based on the various shapes and sizes of containers for dental floss currently available. Although the preferred embodiment relates to currently available shaped containers, in the future, other shaped containers should readily be accommodated by the present invention. The cavity 35 as stated above is configured to resiliently grip a container 40 so that as floss 5 is dispensed from the apparatus 10, the container 40 does not move, thereby preventing fouling of the floss 5 within the apparatus 10 and also prevents breakage and the resulting hassle of rethreading the floss 5. Furthermore, the apparatus 10 ensures the ease of dispensing dental floss 5 without tangling or being exposed to unsanitary conditions. The contours shown in FIGS. 4-8 are intended to functionally receive variously shaped containers 40 without conflict with the other contours for other shaped and sized containers 40.

In FIG. 9, generally rectangular shaped containers 40 (each shown in phantom) are received and positioned within cavity 35 of apparatus 10. Similarly, in FIG. 10 hexagonally shaped, rectangular and cube shaped containers 40 (each shown in phantom) are likewise shown received and positioned within cavity 35 of apparatus 10.

FIG. 11 is a rear cross-sectional view of one of the preferred embodiments supporting a spool 45 of dental floss 5. The spool 45 is supported and retained by a fastening means which may consist of a threaded shaft 50 which is coaxially positioned within said spool 45 and retained by retainer or wing nut 55. Shaft 50 is threaded along its entire length so as to accommodate spools 45 of various lengths.

FIG. 12 is a partial perspective view of an alternative embodiment of the present invention configured as a clamp-type holder 60. A guide rail 65 is positioned usually in a horizontal direction with adjustable steps 70 formed therein to hold and retain gripping arms 75. Gripping arms 75 with gripping means 77 complement each other in gripping and supporting variously shaped containers 40. A rectangular container 40 is only partially shown. A resilient material is shown contained within gripping arms 75. It is intended, though not required, that clamp-type holder 60 be positioned within and between front housing 25 and rear wall 30 for mounting on a vertical surface 15.

FIGS. 13 and 14 depict alternative embodiments of the present invention. In FIG. 13, a universal cavity-type embodiment is shown. A conventional dental floss container 40 is retained and supported (shown in a floating state) by a resilient material which is partially housed in a wall mountable backing 80. Backing 80 may be configured with locking screw guides 85 on each side (only two shown) or by some other conventional vertical surface or wall fastening method. A front retaining housing 90 is shown with a resiliently biased retaining means 95 which is biased by springs 100 or other conventional biasing means. Rear wall retaining means 120 is affixed to backing 80 and holds and supports container 40. Finger and hole catches 105 are used to removably retain housing 90 to backing 80. Bottom hinging arms and holes 110 likewise removably retain housing 90 to backing 80. FIG. 14 is a cross-sectional view of bottom hinging arms and holes 110.

The operation of the above described embodiments is simply and effectively described as follows. A conventionally shaped floss container 40 is positioned into cavity 35 such as shown in FIGS. 9 and 10 and retained in cavity 35. Alternatively, a spool of floss 45 is axially mounted on shaft 50 and retained by nut 55. Floss 5 is threaded through guide 12, opening 7 and cutter 20. Front housing 25 is closed by complementary fitting against rear wall 30. The user grasps the floss 5 by hand from apparatus 10 through opening 7 and out of container 10 and detaches the desired amount for use by cutter 20.

The clamp-type embodiment as shown in FIG. 12, retains and supports a variously sized container 40 between gripping arms 75 by manually adjusting arms along guide rail 65 by adjustable steps 70. The floss 5 is dispensed in the same fashion as described above.

The effective dental floss holder of the present invention encourages dental floss use in accordance with good dental hygiene practices by being a familiar and convenient bathroom accessory.

While the foregoing has presented only a few of the various embodiments of the present invention and it is understood that these embodiments have been presented by way of example only. For example, a timing device or alarm device to serve as a reminder to floss daily. It is expected that others will perceive differences which, while bearing from the foregoing, do not depart from the spirit and scope of the invention herein described and claimed.

What we claim:

1. A dental floss container holder and floss dispenser for dental floss, comprising:
   a housing, said housing having a front and back portion, said front and back portions each having an interior and exterior and defining an interior;
   contoured resilient means for retaining various shaped dental floss containers inside the exterior of said housing, said retaining means affixed to the interior of said back portion of said housing;
   guide means for directing floss from the dental floss container retained within said contoured retaining means to the exterior of said front and back portions of said housing;
   cutting means for detaching the floss said cutting means positioned on the exterior of said front portion of said housing; and
   releasable fastening means for fastening said front and back portions of said housing together.

2. The invention of claim 1, wherein said housing is wall mountable.

3. The invention of claim 1, wherein said retaining means is comprised of open cell foam.

4. The invention of claim 1, wherein said retaining means is comprised of closed cell foam.

5. The invention of claim 1, wherein said retaining means is comprised of neoprene.

6. The invention of claim 1, wherein said retaining means is configured to retain an elongated axial spool of dental floss.

7. A dental floss container holder and floss dispenser for dental floss, comprising:
   a polygonal shaped housing, said housing having an interior and an exterior;
   access means for affording access within said polygonal shaped housing;
   contoured retaining means configured to accommodate variously shaped and sized dental floss containers by successively smaller or larger openings, said contoured retaining means positioned within said housing;
   guide means for directing floss from the container retained within said contoured retaining means from the interior of said housing to the exterior of said housing; and
   cutting means for detaching the floss from the dental floss container holder and floss dispenser, said cutting means positioned on the exterior of said housing.

8. The invention of claim 7, wherein said housing is wall mountable.

9. The invention of claim 7, wherein said retaining means is comprised of open cell foam.

10. The invention of claim 7, wherein said retaining means is comprised of closed cell foam.

11. The invention of claim 7, wherein said retaining means is comprised of neoprene.

12. The invention of claim 7, wherein said retaining means is configured to retain an elongated axial spool of dental floss.

13. A dental floss container holder and floss dispenser for dental floss, comprising:
   a polygonal shaped housing, said housing having an interior and an exterior;
   access means for affording access within said polygonal shaped housing;
   at least two gripping arms which are horizontally adjustable to retain variously shaped dental floss containers;
   guide means for directing floss from the container retained within said retaining means from the interior of said housing to the exterior of said housing; and
   cutting means for detaching the floss from the dental floss container holder and floss dispenser, said cutting means positioned on the exterior of said housing.

14. The invention of claim 13, wherein said housing is wall mountable.

15. The invention of claim 13, wherein said gripping arms are comprised of closed cell foam.

16. The invention of claim 13, wherein said gripping arms are comprised of open cell foam.

17. A dental floss container holder and floss dispenser for dental floss, comprising:
   a housing, said housing having a front and back portion, said front and back portion each having an interior and exterior;
   resilient means for retaining variously shaped containers, said retaining means affixed to the interior of said back portion of said housing;
   retaining plunger means affixed to the interior of said portion of said housing, said plunger means is biased away from said housing such that when said front and back portions of said housing are complementary fastened together, said plunger means forces the container against said resilient retaining means;
   guide means for directing floss from the container retained within said contoured retaining means to the exterior of said front and back portion of said housing;
   cutting means for detaching the floss said cutting means positioned on the exterior of said portion of said housing; and
   releasable fastening means of fastening said front and back portions of said housing together.

18. A dental floss container holder and floss dispenser for dental floss, comprising:
   a housing, said housing having a front and back portion, said front and back portion each having an interior and exterior, said housing is wall mountable;
   resilient means for retaining variously shaped containers, said retaining means affixed to the interior of said back portion of said housing;
   retaining plunger means affixed to the interior of said portion of said housing, said plunger means is biased away from said housing such that when said front and back portions of said housing are complementary fastened together, said plunger means forces the container against said resilient retaining means;
   guide means for directing floss from the container retained within said contoured retaining means to the exterior of said front and back portion of said housing;

cutting means for detaching the floss said cutting means positioned on the exterior of said portion of said housing; and releasable fastening means of fastening said front and back portions of said housing together.

* * * * *